United States Patent [19]

Kott

[11] Patent Number: 4,674,484

[45] Date of Patent: Jun. 23, 1987

[54] LUMBAR TRACTION DEVICE HAVING STAND SEPARATE FROM BED WITH COUNTER-BALANCING WEIGHTS

[76] Inventor: Joseph A. Kott, 408 Marquerite Rd., Metairie, La. 70003

[21] Appl. No.: 827,806

[22] Filed: Feb. 6, 1986

[51] Int. Cl.[4] ......................... A61F 5/04; F16M 11/32

[52] U.S. Cl. ....................................... 128/75; 128/69; 248/164

[58] Field of Search ....................... 128/78, 69, 75, 82, 128/84 R, 89 R; 248/164, 432, DIG. 10

[56] References Cited

U.S. PATENT DOCUMENTS

| | | | |
|---|---|---|---|
| 2,658,506 | 11/1953 | Haskell | 128/75 |
| 2,796,061 | 6/1957 | Miller | 128/75 |
| 2,845,317 | 7/1958 | Orman | 311/79 |
| 2,957,736 | 10/1960 | Olander | 311/83 |
| 3,398,742 | 8/1968 | Alexander | 128/75 |
| 3,452,747 | 7/1969 | Varco | 128/75 |
| 3,503,390 | 3/1970 | Peters | 128/75 |
| 3,522,802 | 8/1970 | Morton | 128/75 |
| 4,492,224 | 1/1985 | Singleton | 128/75 |

*Primary Examiner*—Edgar S. Burr
*Assistant Examiner*—Tonya Lamb
*Attorney, Agent, or Firm*—C. Emmett Pugh; Mason Campell

[57] ABSTRACT

A lumbar traction system particularly suitable for home use, which includes a stand formed by an upper "H" frame member sitting on a pair of spaced, pivoting "X" type legs, with the stand being located near but spaced from the foot of the patient's bed with rope(s) extending from a traction belt or sling worn by the patient to the top, central part of the stand. Centrally located traction weights are suspended on the rope(s) within the stand between the "X" legs, with rearwardly placed, supplemental stabilizing weights (e.g. a water bucket or water bags) being added at the rear of the stand. Such an arrangement is highly stable and self-sustaining, notwithstanding the substantial resistive force of the patient under lumbar traction, and the substantial weight of the centrally located traction weight. A series of opposed sets of hooks are included on the underside of the "H" frame member to be selectively engaged by the cross-bars of the "X" leg frame member for varying the effective height of the stand. A further embodiment for the counter-balancing, stabilizing weights includes a hinged tray (FIG. 3) connected to the backside of the "X" frame member.

11 Claims, 4 Drawing Figures

LUMBAR TRACTION DEVICE HAVING STAND SEPARATE FROM BED WITH COUNTER-BALANCING WEIGHTS

BACKGROUND OF INVENTION

1. Field of Invention

The present invention relates to a traction system and more particularly to a traction system suitable for home, i.e. non-hospital use. The present invention further relates to such a system which utilizes a traction weighing system in which the lines to the weights are suspended over a stand positioned near, but not needing any support, from the foot of the patient's bed.

2. Prior Art and General Background

Neurosurgeons see many patients with cervical and lumbo-sacral pain. A standard initial treatment for these problems is traction.

For the cervical spine there are several commercially available devices which allow this treatment to be undertaken at home. These employ straps placed beneath the chins and occiput (back of head) with a pulley attached to a door. Plastic containers filled with water or sand attached to a rope provide the traction.

For the patients with lumbo-sacral pain a waist band is fitted around the hips, and ropes are attached to this waist band. Using pulleys, traction is applied by attaching the ropes to metal discs or plastic containers containing water or sand. Recently electrical devices have also been employed. For the most part this requires hospitalization or daily trips to the physical therapist.

Although there are several devices currently available for home lumbar traction, these are unsatisfactory and rarely ordered by physicians. One of these commercially available home devices fits onto the edge of a mattress. (Beds without an exposed mattress edge are unsuitable for this type of device.) These devices are far from ideal and leave much to be desired. The weight necessary to attain traction causes the device to tilt and pull away from the mattress. Another type employs a free standing pole attached to a heavy metal base. This apparatus is bulky and awkward to store. Manipulating the heavy metal stand can be difficult for the patient. These also have a tendency to tilt.

Recently various devices that hang the patient by his feet, torso, pelvis, or arm pits have become commercially available. One of these devices requires the user to lay on the floor with a strap between the legs attempting to use the patient's own weight to provide traction. These all require a rather large area for usage. They are relatively expensive and immobile devices. There also may be some medically deleterious effects with some, particularly those hanging the patient by the feet.

The apparatus currently used in hospitals can be obtained for home use. This generally is rented. A hospital bed is necessary to satisfactorily accommodate this equipment. It cannot be directly attached to most patients' beds. These attachments also can be quite cumbersome and expensive.

Suffice it to say that there is no home lumbar traction device currently available in the marketplace that meets both the needs and expectatons of the physician and the patient. A partial list of these needs are as follows:

(1) Portability;

(2) Universality (usable with any type and height bed, without damage to the bed);

(3) Stability (elimination of tipping over and tilting);

(4) Simplicity of structure and assembly;

(5) Minimal space required (both for use and storage); and (6) Affordability

With respect to the patent literature a number of traction devcices are suggested, particularly in the time period of 1955-1970.

These prior devices appear to fall into two basic classes—a first one in which the pulley(s) for the traction weights(s) is/are located either directly or indirectly on the patient's bed frame; note particularly the patents to Morton (U.S. Pat. No. 3,522,802 issued Aug. 4, 1970) and to Singleton (U.S. Pat. No. 4,492,224 issued Jan. 8, 1985). A second approach is that using a separate, free-standing stand located adjacent to the patient's bed; note particularly the patents to Miller (U.S. Pat. No. 2,796,061 issued June 18, 1957) and to Peters (U.S. Pat. No. 3,503,390 issued Mar. 31, 1970). The patent to Alexander (U.S. Pat. No. 3,398,742 issued Aug. 27, 1968) discloses somewhat of a hybrid device in that it utilizes a stand, but one which has to be located flush up against the bed frame, receiving part of its stability from that interface.

The present invention does not attach to the bed nor is any part of it placed under the bed or mattress. The device patented by Alexander has a bar that fits beneath the foot of the bed. Such a device could not be used with the large number of beds that sit flat on the floor. This is also true of the device patented by Miller. (Note FIG. 1 of U.S. Pat. No. 2,796,061.) Based on the drawings of the prior patents and what is known about lumbar traction devices, all of the prior art devices are subject to tilting and/or sliding if an attempt is made to use them as a lumbar traction device. Indeed none are disclosed for specific use as a lumbar traction device.

The most pertinent patents appear to be the patents to Miller and Peters, both of which are directed to "home" type traction systems. The Miller device uses a squared-off frame base located on the floor with a portion of its extending under the patient's bed and having a rearwardly offset pulley section for the traction weight; while the Peters device utilizes a tripod support frame, the apex of which is located above the tensioning line, with the pulleys for the weights being centrally located. Neither use supplemental stabilizing weights for the stand. Both of these stands are vertically adjustable by the use of telescoping supports legs.

There are substantial structural and methodology differences between the stand of the invention and the stands of Miller and Peters, with for example the invention using preferably pivoting "X" braces with the traction weights being centrally located and with the addition of rearwardly placed supplemental stabilizing weights.

It is noted that the Miller device is not a lumbar traction device, but rather an extremity traction device, and could not operate as one due to its inherent instability and tendency to tip over under the greater forces that occur in a lumbar traction device. The Miller device was designed and used for extremity traction, that is, arms and legs. Patients with broken bones of the arms and legs are frequently placed in such devices.

The device patented by Peters, at the weight levels providing the customary angle of traction, tilting would occur as well. In column 4 (Claim 1) of the Peters patent, this limitation is indirectly addressed. If the rope 56 is not horizontal and very near the mattress, the device will tilt towards the bed even under relatively small traction loads such as thirty pounds as arise in extremity traction. It may tilt even when horizontal when the traction loads of for example thirty-five to forty-five pounds as arise in lumbar traction. If the Peters device works at all, it would be limited to beds in which the rope could be kept horizontal and close to the bed and used at relatively low load levels. If a patient's bed had a foot board or frame rising above the level of the mattress, the rope could not be kept horizontal, and tilting would occur.

In addition to universality, the "X" support frame's back bar of the present invention allows the stabilizing-counter balancing weight to be attached. By using the "X" support frame with the counter balancing weight, stability can be achieved with any bed style or angle of traction. The concept of using counter balancing weight, much less a practical means to deploy the idea, is not even remotely present in any of the patented devices, only traction weights being present.

None of the prior art devices employs a structure like the "H" support frame of the invention. Whatever similarities between the "X" support frame and other frames which might be conjured up, none can be applied to the "H" support frame. Likewise, important are the adjustable or multiple "hooks" of the present invention, which allow height adjustment to a given bed height. Also, the cross bar is so placed as to serve the function of bearing the traction weight, without interfering with the counter balancing weight applied to the rear bar of the "X" support frame.

The "H" frame, the "X" frame, and counter-balancing stabilization weight of the present invention are unique individually as applied to lumbar traction and are additionally unique in combination.

The present invention is medically and commercially superior to that of the prior patents.

The patents to Orman (U.S. Pat. No. 2,845,317 issued July 29, 1958) and to Olander et al (U.S. Pat. No. 2,957,736 issued Oct. 25, 1960) are from a non-analogous art and are cited only as examples of tables utilizing "X" bracing type legs.

The Varco patent (U.S. Pat. No. 3,452,747 issued July 1, 1969) is noted only for general background interest in its disclosure of a traction belt.

3. Further General, Summary Discussion of the Invention

The present invention is thus directed to a lumbar traction system particularly suitable for home, i.e. non-hospital, use (although of course it can be used anywhere desired, including the hospital), which includes preferably a stand having an "H" shaped, top frame member sitting on a pair of spaced, pivoting "X" type legs, with the stand being located near but spaced from the foot of the patient's bed, with one or more ropes or lines extending from a traction belt worn by the patient to the top of the stand. Preferably centrally located traction weights are suspended on the rope(s) within the stand between the "X" legs, with rearwardly placed supplemental stabilizing weights (e.g. a water bucket or water bags) being added at the rear of the stand, either as separate hanging items or an integrated tray or platform. Such an arrangement is highly stable and self-sustaining, notwithstanding the substantial resistive force of the patient under traction, and the substantial weight of the centrally located traction weights.

Also preferably included on the top frame member is a series of spaced, opposed hooks on its underside which are selectively mated with the top cross-bars of the "X" legs, to selectively provide the desired effective height to the stand.

The stand and its associated rigging and weights are quite adaptable to many different and varying lumbar traction circumstances, and can be readily and easily altered for various heights and traction forces.

Also, the present invention is not only more flexible and adaptable and reliable than the prior art suggestions, the system is very inexpensive, manufacturable without great investments in plant and equipment, and functions more effectively for the purpose intended than the prior art.

Likewise, the use for the "X" type support legs and a separable "H" frame member makes the system collapsible for compact storage, and the "H" frame being generally flat, with its structure all lying in the same plane, is likewise inherently compact for storage.

Also, although the system is particularly suitable for home use, it could of course also be used in a hospital setting.

BRIEF DESCRIPTION OF THE DRAWINGS

For a further understanding of the nature and object of the present invention, reference should be had to the following detailed desdcription, taken in conjunction with the accompanying drawings, in which like parts are given like reference numerals and wherein.

DETAILED DESCRIPTION OF THE PREFERRED EXEMPLARY EMBODIMENTS

Figure 1:
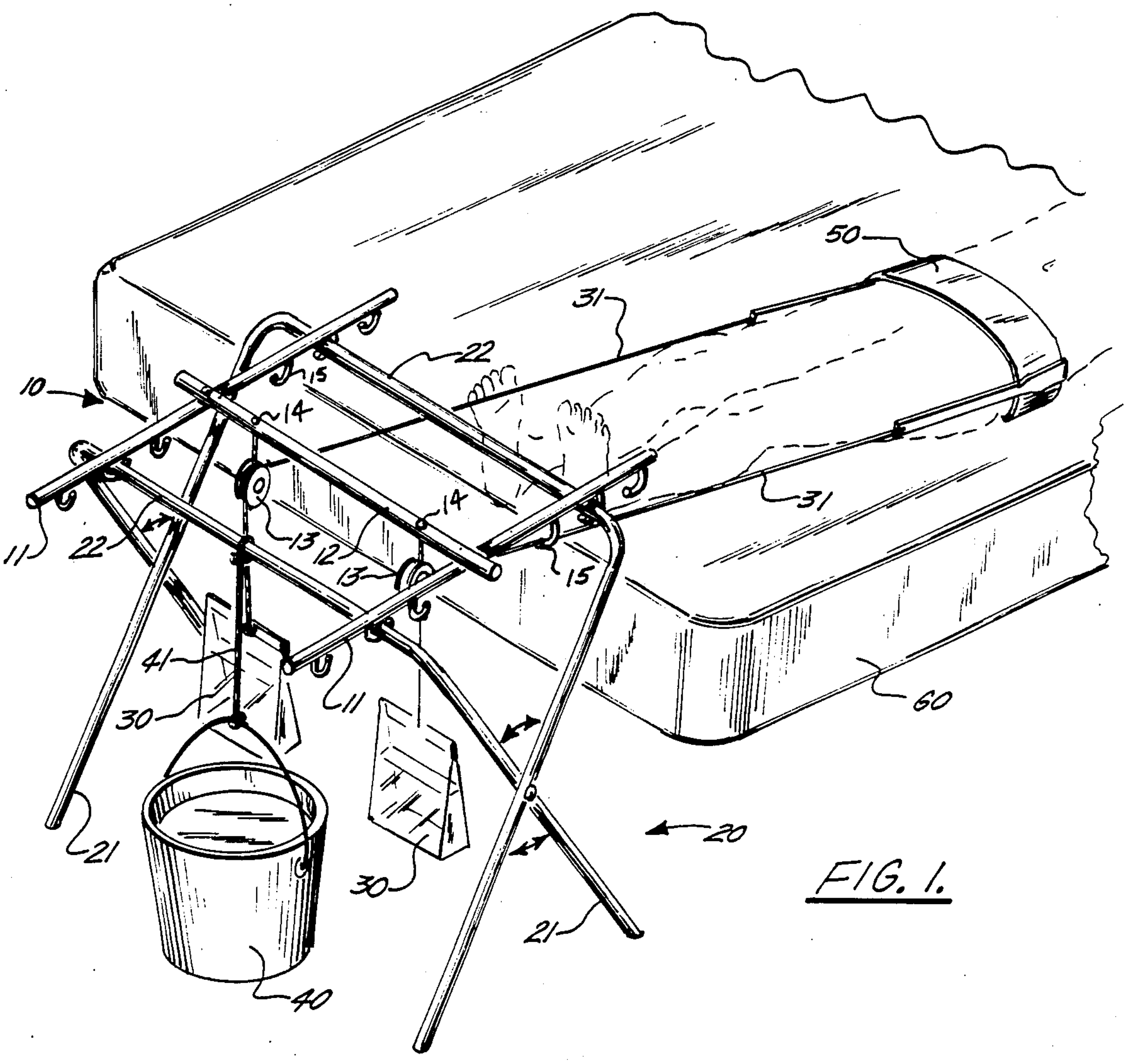
FIGS. 1 is a perspective view of the over-all preferred exemplary embodiment of the traction system of the present invention, showing it in use on a patient lying in bed.
Figure 4:
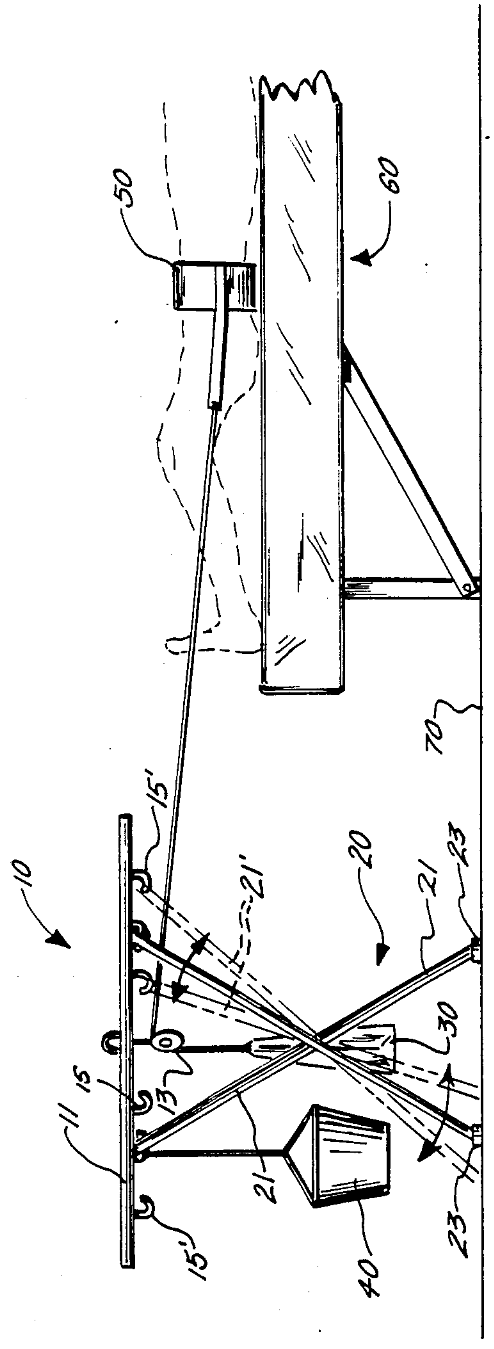
FIG. 4 is a side view of the overall system of FIG. 2.

As can best be seen in FIGS. 1 and 4, the initial, exemplary, preferred embodiment of the overall system of the present invention includes an upper or top frame member 10 and a lower support frame 20. Additionally two weighing sub-systems are use, traction applying weight 30 and a counter-balancing or stabilizing weight 40.

The lower support structure 20 is an aluminum frame as pictured in the figures. This frame 20 is similar in structure to the familiar item—used as the legs for T.V. dinner tables or trays and other such tables. However, its use in a lumbar traction apparatus, as in the present invention, is unique. For lack of a better term it will be referred to as an "X" type support frame. (The legs form the letter "X" when viewed from the side). It is believed that the "X" support frame 20 has not been used in a lumbar traction device prior to this time.

This component 20 of the traction device is light and can be folded easily for storage the "X" support frame 20 includes legs 21 and cross-bars 22. Anti-slip rubber caps 23 (note FIG. 4) are placed over the bottom tips of the four legs. These rubber caps 23 help prevent the "X" support frame 20 from sliding on smooth floors.

"Anti-shift" modifications can also be made in the interfacing between the upper frame member 10 and the lower frame member 20. An elevation or metal attachment or upwardly extending protrusion (not illustrated) on the outer edges of the crossbars 22 of the "X" support frame 20 would be effective in preventing any lateral shifting of the "H" support frame 10 with respect to the legs 21. (The "H" support frame 10 will be described in detail below.) A rubber ring also might be as effective. The point is that a simple retaining device may be attached to the "X" support frame 20, if desired, to prevent lateral slippage of the "H" support frame 10.

The "X" support frame 20 in the preferred embodiment can be for example forty-three (43) inches high (folded) and twenty-two (22) inches wide. Naturally, this height and width could be varied to attain an even greater range of utility.

The apparatus that is used to selectively determine the height of the stand, namely the upper frame member 10, holds the "X" support frame 20 by the hooks 15, as explained more fully below, in position and carries the pulleys 13 for the traction weights 30, is referred to as the "H" support frame 10. (It looks like the letter "H" when viewed from the top or in plan view.) In the preferred embodiment actually built, hollow aluminum pipe or tubing was used for both the "sides" 11 and the crossbar 12 of the "H" support frame 10. (Note FIG. 1.) Alternatively, flat pieces or plates of metal could be used for either the side members or the crossbar or both. The crossbar 12 can be fixed to the sides 11 at their mid-points with for example bolts. This could also be accomplished with for further examples welding or interlocking grooves.

The two laterally spaced pulleys 13 are attached to the "H" support frame 10 with hanging eyelets 14. Welded or clamped pulleys could be sustituted. The pulleys 13 in the figures of the preferred embodiment are relatively inexpensive. Higher quality pulleys with rigid fixation to the "H" support frame 10 might be desirable for a commercial product.

The exemplary length of the sides 11 of the "H" support frame 10 in the preferred embodiment is twenty-six and a half ($26\frac{1}{2}$") inches long.

The series of "hooks" 15 that are selectively used to attache the "H" support frame 10 to the "X" support frame 20 can be seen in FIGS. 1 and 4. In the preferred embodiment actually built, these hooks 15 were made from pipe braces attached to the underside of the "H" support frame 10 with metal screws. The preferred embodiment illustrated has three exemplary sets of opposed hooks 15, allowing the selection of three different heights for the overall stand (note phantom lines legs 21′ and the curved direction arrows of FIG. 4).

This hooked interconnection between the two frame members 10, 20 provides good structural stability to the entire unit. As noted, the multiplicity of opposed hook sets 15 are an important feature, because it is the means, not only for interconnecting the two frame members, but also for varying or adjusting the effective height of the overall stand. The more distant hooks 15′ (note FIG. 4) of the "H" support frame 10 will provide the lowest level of the "X" type support frame 20. The more centrally located hooks of the "H" support frame 10 will correspondingly give a greater height to the "X" support frame 20.

The two crossbars 22 of the "X" support frame 20 are simply set inside the hooks on the side bars of the "H" support frame 10 to attain the desired height. This can be appreciated by studying the figures of the "H" support frame 10 and the completely assembled and utilized apparatus illustrated in FIGS. 1 and 4. When the weight of the traction containers is applied, a vertically directed, downward vector gives strength to the entire unit.

As discussed, FIGS. 1 and 4 show multiple sets of opposed, spaced hooks 15 on the underside of the sides 11 of the "H" frame 10. An exemplary alternative would be to have one set of opposed hooks on each side 11, whose positions ae adjustable along the length of the sides 11 of the "H" support frame 10. Also, the length of the "H" support frame 10 could be varied to accommodate more hooks 15 for an even wider range of heights. Likewise, the width of the "H" support frame 10 could be varied to accommodate different widths needed for, for example, more than two spaced tensioning weights 30. Rubber protectors should be placed on all exposed edges of the "H" support frame 10 for protection.

It is believed that the "H" frame support 10 has not heretofore been used in a home lumbar traction device.

One of the major problems encountered with currently available home lumbar traction devices is instability. To date, currently available home lumbar traction devices may tilt and fall in various directions, perhaps even falling into bed with the user. A key and innovative feature of the present invention is the use of counter-weights(s) on the "X" support frame device 20.

This was accomplished in the preferred embodiment actually built and in the embodiment illustrated in FIGS. 1 and 4 by suspending a bucket of water 40 from the back of the "X" support frame 20. This counter balance could be accomplished in a commercial product with, for further example, the sealable water containers 140 shown in FIG. 2. These could be similar to those available and seen used in the preferred embodiment for the traction weights 30 to provide the traction force to the sling or patient belt 50.

Figure 2:
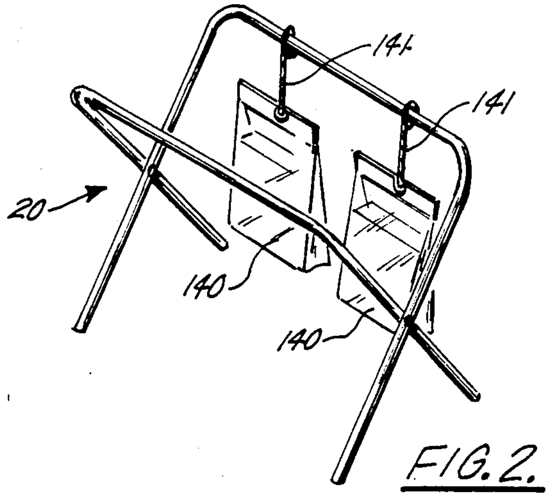
FIG. 2 is a top perspective view of a further exemplary embodiment of the "X" type support frame of the present invention havign a counter-balancing stabilinzing sub-system which includes one or more water bags (an exemplary two being illustrated) in place of the water bucket of the embodiment of FIG. 1.

Thus, ropes or hooks 41, 141 and containers 40, 140 attached directly to the back cross-bar 22 of the "X" support frame 20 (FIGS. 1 and 2) or, as a further exemplary variation, a tray 241 hinged on the base of the back legs (FIG. 3) could be used to hold or attach this balancing weight. FIG. 2 illustrates the back bar 22 of the "X" support frame 20 with two exemplary containers of water suspended from it. This concept and part of this device should not be confused with the water containers 30 hanging from the "H" support frame 10, which supply the weight for the traction force, the two weighing sub-systems 30 and 40 (140) serving two totally different functions.

Figure 3:
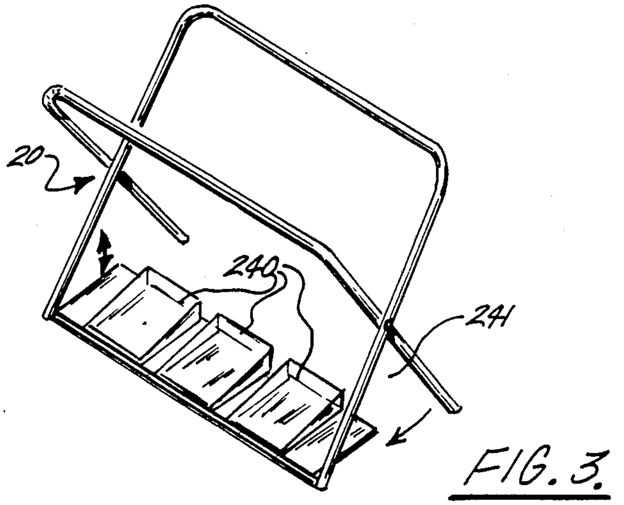
FIG. 3 is a top perspective view of a still further exemplary embodiment of the "X" type support frame of the present invention having a counter-balancing stabilizing sub-system which is integrated into a tray or platform hinged to the backside of the frame.

As noted, FIG. 3 illustrates another means of applying the counter-balancing weight to the "X" support frame 20. An integral tray or platform 241 is hinged to the back legs 21 of the support frame 20. When opened, it sits on the floor, and containers of water 240 are placed on this tray, providing the counter-balancing needed. When closed for storage, the tray 241 is folded flat up against the legs 21, thereby not adding any bulk to the unit when in storage.

Water has been used in the preferred embodiments and in this discussion as the means for applying both the counter balance to the "X" support frame 20 and the traction weight to the belt or sling 50. However, sand, metal discs or other weighty materials could also be used. These materials however would have to be purchased and carried home, while water is available in the home, is inexpensive and easily disposed of for storage of the device.

In use the "X" support frame 20 is placed at the foot of the user's bed. It can abut the bed or stand free, and there is no necessity that the stand receive any support from the patient's bed or extend under the patient's bed, as has been necessary in the prior art. The "H" support frame 10 is placed atop the "X" support frame 20. The multiple hooks 15 or variable position hooks are then used to obtain the appropriate height for the overall stand.

The counter-balancing, anchoring weight(s) 40, 140 is/are attached to the "X" support frame 20. This counter-balancing, anchoring weight can take many forms as discussed earlier. The bucket 40 in the photograph contains for example approximately eighteen (18 lbs.) pounds of water.

Ropes or lines 31 are threaded through the eyes or races of both pulleys 13. These ropes are then attached to the traction weights 30. The figures show this weight being provided by two commercially available containers or bags 30. These containers 30 are marked so that filling to certain marked level provides a given number of pounds of weight. The containers 30 contain for example approximately thirteen (13 lbs.) pounds of water each. Most neurosurgeons use between eight and fifteen (8–15 lbs.) pounds on each side, depending on the user's size. Naturally, the greater the counter-balancing anchoring weight(s) 40, 140, 240, the greater than stability. When two containers 140 with for example approximately twenty (20 lbs.) pounds of water in each are used, approximatey eighteen to twenty (18–20 lbs.) pounds of weight on each side can be used for traction. The counter-balancing weight(s) needed rises in proportion to the traction weight to be applied.

The user or patient puts on a comemrcially available pelvic waist band or sling 50. These are manufactured by several firms and are available at medical and orthopedic supply stores. The band 50 can be in the form of for example a white belt-like device. The user or patient lays in bed, as illustrated in FIGS. 1 and 4, in alignment with the traction unit. The ropes or lines 31, which had been placed on the bed 60, are now attached to the pelvic waist band 50. In doing this, the traction weights 30 are elevated from the floor 70 and lumbar traction is applied to the patient. The ropes or lines 31 are tied to metal rings on the pelvic waist band 50, or alternatively, this could be accomplished with a clap or series of clasps on the end portions of the rope 31.

Pillows or a wedge shaped foam cushion (not illustrated) can be placed beneath the knees to achieve maximum comfort and benefit, if desired.

In conclusion, although particularly suited for home use, the above-described embodiments of course could also be used to administer lumbar traction in a hospital or physical therapy unit setting, when appropriate.

When the traction system is no longer needed, the "H" upper frame member 10 is disconnected from the "X" lower frame member 20, with the latter then being collapsible into a substantially flat disposition. The substantially flat upper frame member 10 can then be placed adjacent to or for example on top of or beneath the collapsed leg frame member 20 for compact storage together. If the embodiment of FIG. 3 is being used, the tray 241 is merely pivoted up about its hinge connections against the back ones of the legs 21. The water is emptied out of for example the bags 30, 140, and everything, including the lines 31 and the belt 50, conveniently stored together in for example a compact box.

The varying embodiments described herein in detail for exemplary purposes are themselves of course subject to many different variations in structure, design and application. Because many varying and different embodiments may be made within the scope of the inventive concept(s) herein taught, and because many modifications may be made in the embodiments herein detailed in accordance with the descriptive requirements of the law, it is to be understood that the details herein are to be interpreted as illustrative and not in a limiting sense.

What is claimed is:

1. A lumbar traction system suitable for use in the home, comprising:
- a stand frame including
  - a bottom frame member including two sets of spaced, pivoted "X" legs connected together by two cross-bars at their tops, the "X" legs collapsing together to form a substantially flat structure for storage and pivoting apart to an operative disposition; and
  - a separable, substantially flat top frame member removably connected to said bottom frame member for support above the floor and having two laterally spaced sides connected together by means of at least one, laterally extended cross-bar, each side having at least one opposed set of hooks extending down from its underside, said two cross-bars of said bottom frame being fitted into said hooks preventing the "X" legs from collapsing together, with said legs supporting said top frame member above the floor at a desired height;
- traction weight means carried by said frame by means of at least one line extending over said frame to a sling connectable to the patient's body for applying lumbar traction force to the patient; and
- counter-balancing weights stabilizing means connected to the rear portion of said frame opposite to the side closest to the patient for counter-balancing the traction force applied by said traction weight means to the patient, effectively preventing said frame from being tipped over by the traction force.

2. The system of claim 1, wherein said upper frame member has an "H" shape.

3. The system of claim 1, wherein the underside of each side of said upper frame member includes a series of spaced, opposed hooks, allowing the effective height of said stand to be adjusted by selectively engaging said two cross-bars of said lower frame member with selected ones of said hook sets.

4. The system of claim 1, wherein said counter-balancing means includes at least one weight suspended from the backside cross-bar of said lower frame member.

5. The system of claim 1, wherein said counter-balancing means comprises:
- a tray hinged to the bottom portions of the back legs of said lower frame member, said counter-balancing weight means placed upon said tray, said tray being moveable from a substantially flat storage disposition up against the legs to which it is hinged and down into supporting contact with the floor when in its operative disposition carrying the counter-balancing weight means.

6. A lumbar traction system suitable for home use, comprising:

a stand mounted on the floor;

traction weight means carried by said stand by means of at least one line extending over said stand to a sling connectable to the patient's body for applying lumbar traction force to the patient; and counter-balancing weight stabilizing means connected to the rear portion of said stand opposite to the side closest to the patient for counter-balancing the traction force applied by said traction weight means to the patient, effectively preventing said frame from being tipped over by the traction force, said counter-balancing means including a tray hinged to the bottom portions of said stand, said counter-balancing weight means placed upon said tray, said tray being moveable from a substantially flat storage disposition up against the stand to which it is hinged and down into supporting contact with the floor when in its operative disposition carrying the counter-balancing weight means.

7. The method of providing lumbar traction to a patient, suitable for use in the home, comprising the following steps:

(a) placing a stand on the floor adjacent to the foot of the bed upon which the patient is lying, said stand being placed from and out of contact with the bed with all of its support structure being located past the end of the bed, (b) suspending substantial traction weight means from said stand for applying a traction force to the patient through at least one line attached between the traction weight means and a sling worn by the patient;

(c) opposing the traction force in the line, the traction force having a force vector along the line generally toward the patient which causes a tilting force to be applied to the stand in a direction toward the patient, with a counter balancing weight means applied in a configuration having the traction weight means positioned between the counter balancing weight means and the patient, which produces a counter force on the stand in a direction away from the patient to negate the tilting force caused by the traction force, (d) providing said stand in the form of a bottom frame member including two sets of spaced, pivoted "X" legs connected together by two cross-bars at their tops, the "X" legs collapsing together for storage, and a separable, substantially flat top frame member removably connected to said bottom frame member for support above the floor, said frame member including two laterally spaced sides connected together by means of at least one, laterally extended cross-bar.

8. The method of claim 7, wherein in step "c" there is included the step of:

suspending the counter-balancing weight means from the backside of said stand.

9. The method of providing lumbar traction to a patient, suitable for use in the home, comprising the following steps:

(a) placing a stand on the floor adjacent to the foot of the bed upon which the patient is lying, said stand being placed from and out of contact with the bed with all of its support structure being located past the end of the bed, (b) suspending substantial traction weight means from said stand for applying a traction force to the patient through at least one line attached between the traction weight means and a sling worn by the patient;

(c) providing a tray hinged to the bottom portions of said stand and counter-balancing weight means placed upon said tray, said tray being moveable from a substantially flat storage disposition up against the stand to which it is hinged and down to an operative disposition into supporting contact with the floor, said tray when in its operative disposition carrying the counterbalancing weight means.

10. The method of providing lumbar traction to a patient, suitable for use in the home, comprising the following steps:

(a) placing a stand on the floor adjacent to the foot of the bed upon which the pateint is lying, said stand being spaced from and out of contact with the bed with all of its support structure being located past the end of the bed, (b) suspending substantial traction weight means from said stand for applying a traction force to the patient through at least one line attached between the traction weight means and a sling worn by the patient;

(c) attaching counter-balanced weight means to the stand on the side distal from the patient, preventing the stand from tipping over despite the substantial traction weight means being applied;

(d) providing said stand in the form of a bottom frame member including two sets of spaced, pivoted "X" legs connected together by two cross-bars at their tops, the "X" legs collapsing together to form a substantially flat structure for storage and pivoting apart to an operative disposition; and a separable, substantially flat top frame member removably connected to said bottom frame member for support above the floor and having two laterally spaced sides connected together by means of at least one, laterally extended cross-bar, each side having at least one opposed set of hooks extending down from its underside, said two cross-bars of said bottom frame being fitted into said hooks preventing the "X" legs from collapsing together, with said legs supporting said top frame member above the floor at a desired height; and when the stand is no longer needed for applying lumbar traction to the patient, disconnecting said bottom and top frame members, collapsing said lower frame member to form a substantially flat structure for storage, and placing said substantially flat top member adjacent to said collapsed lower frame member for storage.

11. The method of claim 10, wherein in step "c" there is included the step of:

suspending the counter-balancing weight means from the backside of said stand.

* * * * *